(12) United States Patent
Zeilinger

(10) Patent No.: US 9,892,233 B2
(45) Date of Patent: Feb. 13, 2018

(54) VISUALIZATION OF A FUNCTIONAL SEQUENCE OF A MEDICAL APPARATUS

(71) Applicant: Thomas Zeilinger, Nürnberg (DE)

(72) Inventor: Thomas Zeilinger, Nürnberg (DE)

(73) Assignee: Siemens Aktiengesellschaft, München (DE)

(*) Notice: Subject to any disclaimer, the term of this patent is extended or adjusted under 35 U.S.C. 154(b) by 767 days.

(21) Appl. No.: 14/453,307

(22) Filed: Aug. 6, 2014

(65) Prior Publication Data
US 2015/0046137 A1 Feb. 12, 2015

(30) Foreign Application Priority Data

Aug. 6, 2013 (DE) .................. 10 2013 215 406

(51) Int. Cl.
*G06F 19/00* (2011.01)
*A61B 6/10* (2006.01)
*A61B 6/00* (2006.01)
*A61B 5/00* (2006.01)

(52) U.S. Cl.
CPC ........ *G06F 19/3412* (2013.01); *A61B 5/0046* (2013.01); *A61B 6/102* (2013.01); *A61B 6/467* (2013.01); *A61B 6/527* (2013.01); *A61B 6/542* (2013.01); *A61B 6/4441* (2013.01); *A61B 6/4464* (2013.01)

(58) Field of Classification Search
None
See application file for complete search history.

(56) References Cited

U.S. PATENT DOCUMENTS

| | | | | |
|---|---|---|---|---|
| 6,272,368 B1* | 8/2001 | Alexandrescu | ........... | A61B 6/08 250/349 |
| 2008/0123811 A1* | 5/2008 | Curtis | .................... | A61B 6/102 378/91 |
| 2013/0185090 A1* | 7/2013 | Kargar | .................. | G06Q 50/22 705/2 |

FOREIGN PATENT DOCUMENTS

DE        10200534 A1        7/2003

OTHER PUBLICATIONS

German Office Action dated Apr. 10, 2014 for corresponding German Patent Application No. DE 10 2013 215 406.2 with English Translation.

* cited by examiner

*Primary Examiner* — Syed Roni
(74) *Attorney, Agent, or Firm* — Lempia Summerfield Katz LLC

(57) ABSTRACT

Visualization of a functional sequence of a medical apparatus includes accepting a mathematical model describing at least the medical apparatus, and accepting a log file. The log file includes at least one value of at least one electrical signal of the medical apparatus during the functional sequence. At least one state variable of the medical apparatus is determined as a function of the mathematical model and the log file, and the at least one state variable of the medical apparatus is visualized.

18 Claims, 4 Drawing Sheets

VISUALIZATION OF A FUNCTIONAL SEQUENCE OF A MEDICAL APPARATUS

This application claims the benefit of DE 10 2013 215 406.2, filed on Aug. 6, 2013, which is hereby incorporated by reference in its entirety.

BACKGROUND

The present embodiments relate to visualization of a functional sequence of a medical apparatus.

Medical devices or apparatuses, such as computed tomograph systems or X-ray equipment, for example, have reached the spatial dimensions of small to medium-sized industrial, mechanical engineering installations. Operators, such as physicians and technical or medical assistants, of such devices may be faced with complex, mechanical, movable components, such as examination tables, lamp supports, monitor racks, robot-like supporting arms, adjustable image detectors and much more. The workflows of medical examinations or interventions are also protracted and complicated sometimes. In addition, the functional sequences that take place within a medical device may not be visible from the outside or take place at a speed that is indiscernible to the human eye. If a medical apparatus malfunctions or, for example, a component of the medical apparatus collides with another medical device during a workflow, it is often difficult or even impossible to reproduce afterwards the manner in which this situation may have arisen. This issue may arise with the diagnosis of faults that occur inside a medical device, and as a solution, log files, in which parameters of the medical device (e.g., stress states of certain voltage nodes) are recorded, may be introduced. In practice, however, a very high level of expertise and knowledge of the functioning of the medical device is required in order to be able to draw meaningful and accurate conclusions from these log files. If necessary, such log files are also sent to a technical department of the manufacturer of the medical equipment for evaluation as standard practice today.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for visualization of a functional sequence of a medical apparatus is provided in order to make the functional sequence more intuitively understandable than a log file has in the prior art.

A method for visualization of a functional sequence of a medical apparatus includes acceptance of a mathematical model at least describing the medical apparatus, and acceptance of a log file. The log file includes at least one value of at least one electrical signal of the medical apparatus during the functional sequence. The method also includes determination of at least one state variable of the medical apparatus as a function of the mathematical model and the log file, and visualization of the at least one state variable of the medical apparatus.

A functional sequence may be the performance of a measurement, a period of time during a medical examination of an object, or sequences in a medical intervention. In addition, a functional sequence may include a motion sequence or a sequence of at least one input/output or procedures inside the medical apparatus.

In act S1, a mathematical model that at least describes the medical apparatus is accepted, loaded or obtained. Mathematical models are known and are, for example, already created during the development of a medical apparatus. Using mathematical formulae and correlations, for example, mathematical models describe the internal functioning, the mechanical performance or other aspects of the performance of the medical apparatus. Mathematical models may include parameters, input variables, output variables and combinations of the aforementioned variables. For example, a simple mathematical model of a manually movable patient table may include the geometrical dimensions and parameters of a built-in electrical distance sensor. Based on the input variable of the distance sensor (e.g., of an electrical voltage) with the aid of the mathematical model, the position of the patient table may be determined as an output variable. Depending on requirements, various mathematical models that may differ in nature and the level of detail may be used.

In act S2, a log file is accepted, loaded or obtained. A log file may be logs, such as network logs, input/output logs, standardized, such as AXCS telegrams, or proprietary logs. The log file includes at least one value of at least one electrical signal of the medical apparatus during the functional sequence. In the exemplary embodiment of the manually moveable patient table, the value of an electrical signal may be the voltage of the electrical distance sensor. The value of an electrical signal may be a measured value.

In act S3, at least one state variable of the medical apparatus is determined as a function of the mathematical model and the log file (e.g., at least one state variable of the medical apparatus is determined as a function of the at least one value of the at least one electrical signal of the medical apparatus during the functional sequence). In the exemplary embodiment of the manually moveable patient table, the state variable of the medical apparatus may be the position of the patient table that is determined as a function of the mathematical model and the log file, for example, with the specific value of the electrical signal (e.g., with the voltage of the electrical distance sensor).

In act S4, the at least one state variable of the medical apparatus is visualized. The visualization or representation of the state variable may, for example, take place with the aid of a monitor in the form of text output, a diagram or a graphic.

The visualization of the at least one state variable of the medical apparatus may include a graphical image of the mathematical model.

Depending on the kind of mathematical model, the graphical image, which may also be a graphical representation, may differ. For example, the graphical image of the mathematical model of the manually moveable patient table may be a cuboid object with the marking of an original position. The position of the patient table is determined as a function of the mathematical model and the voltage level of the electrical distance sensor from the log file, and the graphical image of the mathematical model and/or of the medical apparatus that is represented by the mathematical model is adjusted and visualized. In this example, the result is the cuboid object shown, which assumes a position corresponding to the log file. For example, if the mathematical model is a movement model (e.g., the mathematical model serves to describe a movement of the medical apparatus), it may be advantageous to make the graphical image or the representation of the mathematical model selectable, for example, using a predeterminable zoom factor and/or a predeterminable angle of view to the image displayed.

In an advantageous development, the medical apparatus includes an imaging system.

In connection with imaging systems, one or more of the present embodiments may be used advantageously, as current imaging systems such as computed tomography systems, X-ray systems or magnetic resonance imaging systems may include movable parts. Movement of the movable parts is to be monitored and reproduced. An additional aspect includes inputs by users of an imaging system and the reaction of the system to these inputs.

In a further embodiment, the log file includes a time sequence of the at least one value of the at least one electrical signal of the medical apparatus during the functional sequence, and the acts S3 and S4 are repeated for selectable points in time.

This provides that the log file includes a plurality of values (e.g., in the form of a table), where the values may each be assigned to a time. By repeating the method act S3, the determination of at least one state variable of the medical apparatus as a function of the mathematical model and the log file (e.g., of the at least one value of the electrical signal at a predeterminable time), and method act S4, the visualization of the at least one state variable of the medical apparatus, the time sequence of the state variable of the medical apparatus may be displayed.

In one embodiment, the method is repeated until a termination criterion is met (e.g., the accomplishment of a predeterminable number of method cycles or the accomplishment of a predeterminable duration or the activation of a button or the activation of a switch or the accomplishment of the last entry of the log file). In other words, the method is concluded when a termination criterion that is verified in accordance with method act S4 is met.

The mathematical model may also include an object outside the medical apparatus.

In other words, the mathematical model may include additional information about movable or immovable objects in the room Immovable objects may, for example, be walls, installations, immovable equipment such as monitor racks, pillars, etc. Movable objects may, for example, be equipment that executes a deterministic movement, like a rotating fan, people, robots or movable equipment, such as movable instrument tables. With this feature, for example, rooms may be modeled by including the architecture of the walls of the rooms in the mathematical model.

A further advantageous embodiment provides that in addition, the log file includes at least one value describing the additional object.

If the log file includes a value that describes the additional object, a state variable may be calculated with the aid of the mathematical model and this value. For example, the additional object may be a person, and the additional value may describe the position of this person. A mathematical model that describes the position of a C-arm of an X-ray machine and of the person may calculate the position of the C-arm in relation to the person using a value of the medical apparatus during a functional sequence and the additional value of the additional object (e.g., in this case, the position of the person).

In an alternative embodiment, the mathematical model includes a collision model. The collision model determines a collision value, where the collision value determines the probability of a collision of the medical apparatus with the additional object.

In an embodiment of a method, the method serves to review a sequence of movements of a medical apparatus (e.g., the evaluation of a possible collision between a mechanical component of the medical apparatus and a movable or immovable object). The creation of a collision model is a method known, for example, from robotics. Collision models use input variables such as, for example, the positions and the movement of mechanical components to calculate whether a collision with objects has taken place or will take place during the period under observation. In this embodiment of the method, the collision model determines the probability of a collision of the medical apparatus with the additional object. The determined probability, which may also be described as the collision value, may be presented on a presentation medium (e.g., on a monitor). Values of the collision value may, for example, be 1 for a collision that has occurred, 90% for a rapid movement of a mechanical component of a medical apparatus toward a wall, or 0.1% for a slow movement of a mechanical component of a medical apparatus, where the mechanical component is still relatively far from a collision object (e.g., a wall) but may in principle hit the collision object.

Advantageously, the log file is extended by a predeterminable value of at least one electrical signal of the medical apparatus and/or by a value describing the additional object.

This feature makes it possible to simulate scenarios without actually performing the scenarios. For example, the output signal of a foot switch may be predetermined, and/or an actual output signal of the foot switch is overwritten with a predeterminable value to thus simulate the performance of the medical apparatus as a function of this predetermined value.

In one embodiment, a device for the visualization of a functional sequence of a medical apparatus includes an arithmetic unit and an output unit. The arithmetic unit is configured to accept a mathematical model at least describing the medical apparatus. The arithmetic unit is also configured to accept a log file, where the log file includes at least one value of at least one electrical signal of the medical apparatus during the functional sequence. The arithmetic unit is configured to determine at least one state variable of the medical apparatus as a function of the mathematical model and the log file, and to convert the at least one determined state variable of the medical apparatus into a visualization signal and to make the visualization signal available to the output unit. The output unit is configured to accept and to visualize the visualization signal.

The arithmetic unit may be configured as a computer including a processor, for example, that has an appropriate interface for the acceptance of the mathematical model of the medical apparatus and the log file, and processes a computer program in order to determine the at least one state variable of the medical apparatus as a function of the mathematical model and the log file and to convert the at least one state variable into a visualization signal. The visualization signal may be transferred to the output unit (e.g., a computer monitor), and the output unit visualizes the at least one state variable.

In an embodiment, the device is configured to execute one of the methods discussed above.

The device may, for example, be equipped with a corresponding computer program that processes the individual method acts. In the case of a method that is repeated, the device may be equipped with an input device (e.g., a button), the switching state of which forms a termination criterion. Thus, for example, an activated button may be interpreted as a fulfilled termination criterion. If the method according to one or more of the present embodiments includes a method act in which the log file also includes at least one value describing an additional object (e.g., the coordinates of a movable object, such as an operator), then the device may include a device for recording the coordinates of the movable object. Such device may, for example, be one or more cameras that record an operator. From the images of the one or more cameras, the coordinates of the operator may be determined.

DETAILED DESCRIPTION

Figure 1:
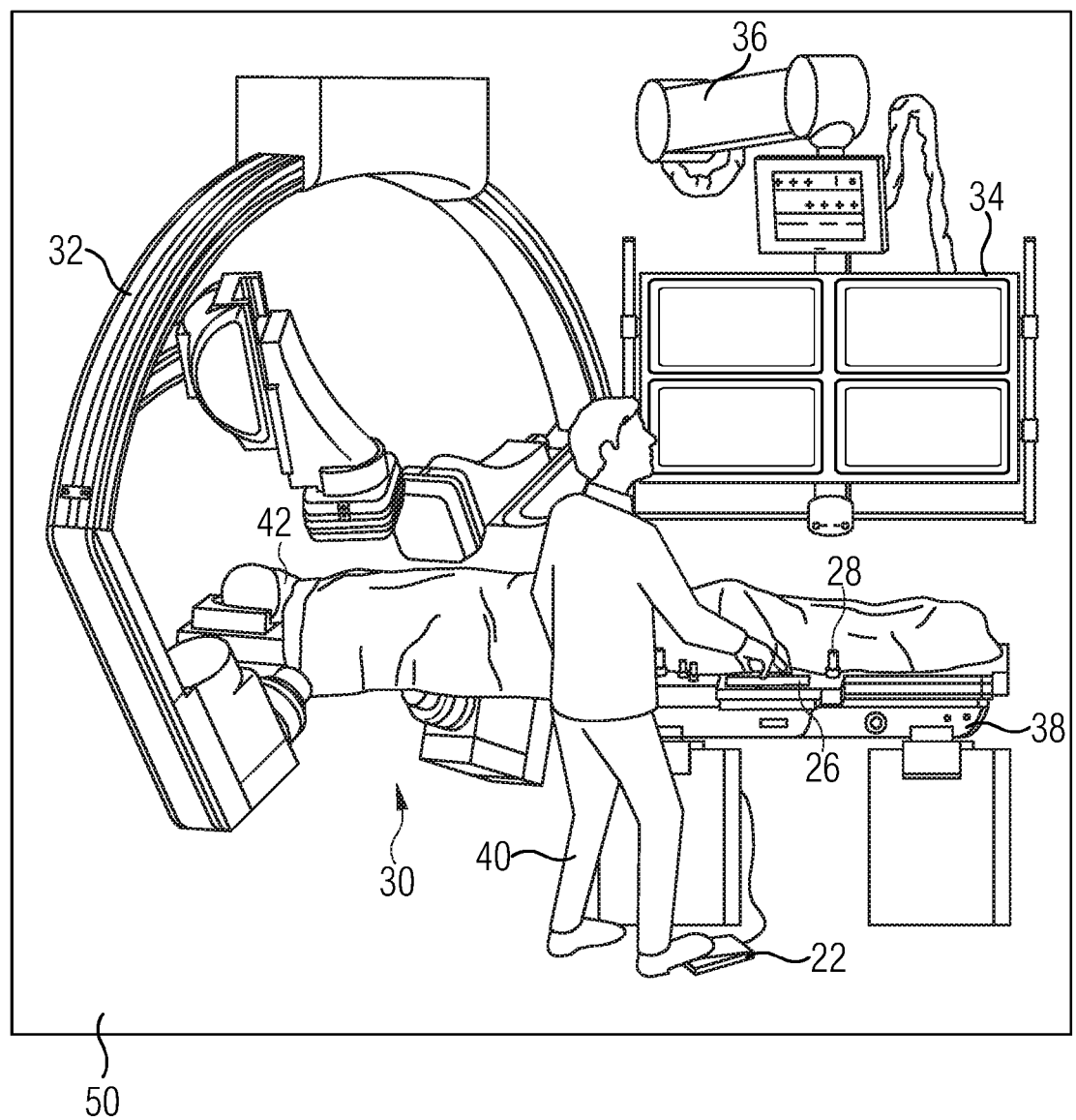
FIG. 1 shows an operating room with a plurality of medical devices according to the prior art.

FIG. 1 shows an exemplary and diagrammatic view of an operating room 50 with a plurality of medical devices according to the prior art. A medical apparatus 30 (e.g., a two-level X-ray device), in which an X-ray source and an X-ray detector are arranged opposite each other on a C-arm 32, is shown. The C-arm 32 is movably connected to the ceiling of the operating room 50 by a ceiling mount. The two-level X-ray device is used, for example, for examination of a human patient 42 who is positioned on a movable patient table 38. Images of the patient 42 may be displayed on a monitor rack 34 that may be positioned by an articulated arm 36. An operator 40 (e.g., a physician) may operate the medical apparatus 30, the patient table 38 and the monitor rack 34 by various control elements, such as a foot switch 22, a joystick 28 or an input device 26 (e.g., alter a position of a component of the devices using a motor, set parameters or obtain X-ray images). Modern medical devices may also be able to carry out motion or functional sequences automatically or semi-automatically, for example, for organ programs. This example shows that a modern operating room may include a plurality of different medical devices that interact with each other. If unintended behavior occurs in the course of an examination (e.g., if the C-arm 32 collides with a mounting bracket of the monitor rack 34), it may be advantageous for an operator of the operating room to reproduce the sequence of the collision in order to obtain a remedy where necessary.

Figure 2:
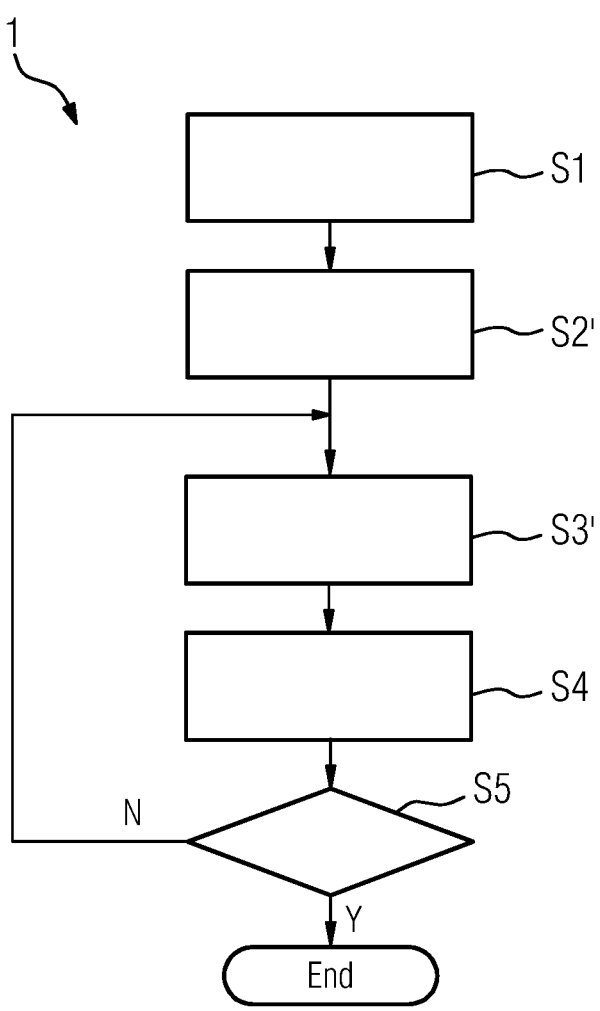
FIG. 2 shows a flow chart of one embodiment of a method for visualization of a functional sequence of a medical apparatus.

FIG. 2 shows a flow chart of one embodiment of a method 1 for the visualization of a functional sequence of a medical apparatus. The method 1 includes method acts S1 to S5. The method starts with act S1 and ends, "End", after act S5. The individual acts includes: S1) accepting (e.g., receiving) a mathematical model describing at least the medical apparatus; S2') accepting a log file, where the log file includes at least one value of at least one electrical signal of the medical apparatus during the functional sequence and includes a time sequence of the at least one value of the electrical signal of the medical apparatus during the functional sequence; S3') determining at least one state variable of the medical apparatus as a function of the mathematical model and of the at least one value of the at least one electrical signal of the medical apparatus at a selectable point in time; S4) visualizing the at least one state variable of the medical apparatus; and S5) interrogating a termination criterion and if the termination criterion is met, ending, "End", the method; otherwise, skipping to act S3'.

For the first processing of act S3', for example, the time may be set to the first time of the log file, where the associated at least one value of the at least one electrical signal of the medical apparatus is determined. Every time act S3' is skipped to, the selectable point in time is increased by one time step. The time step is provided by the time sequence of the log file until the last time is reached. The interrogation or testing of the question as to whether the last time of the log file is reached thereby forms the termination criterion. In this way, the log file will run step-by-step from the first time to the last time.

Figure 3:
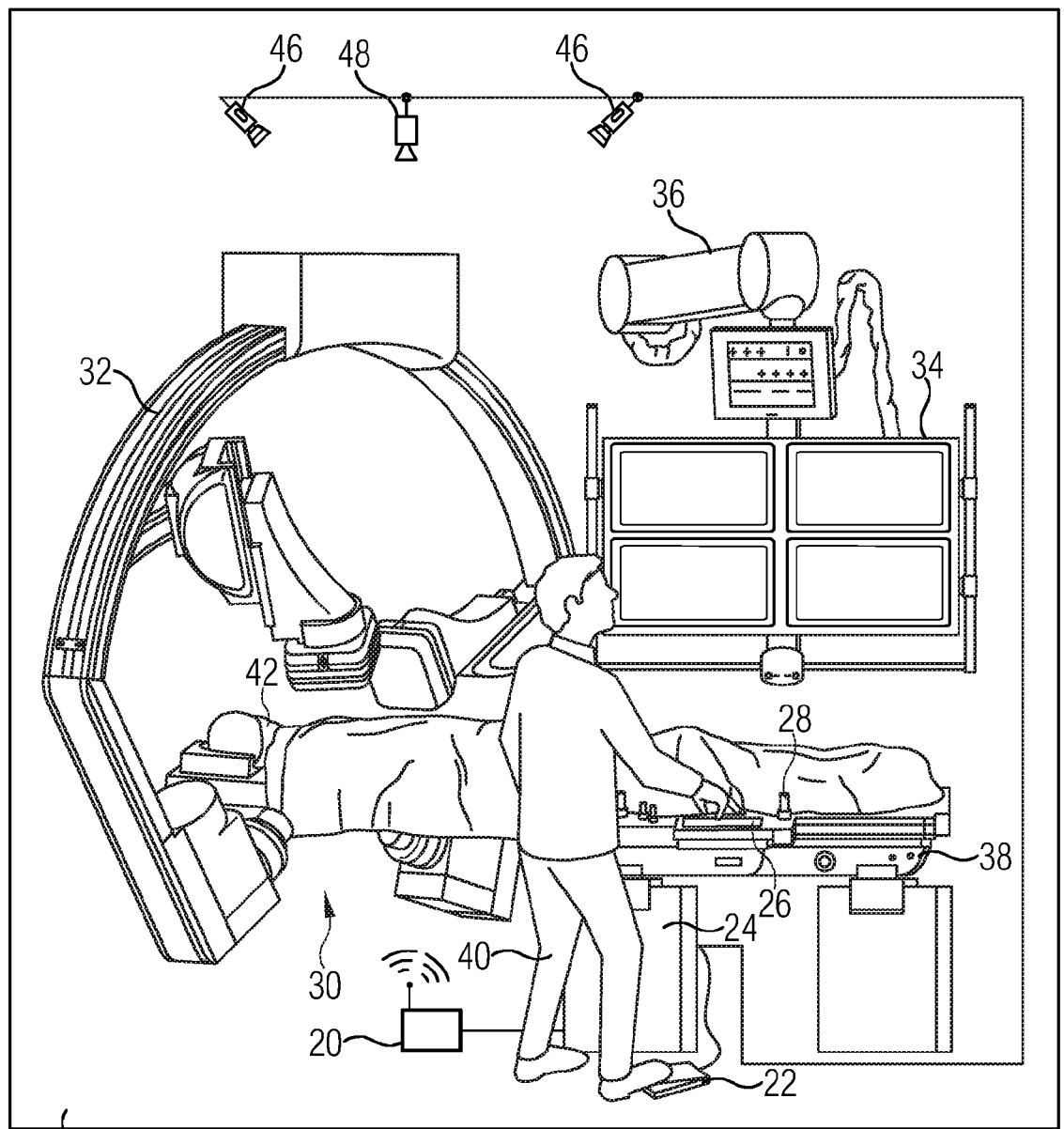
FIG. 3 an operating room with a plurality of medical devices and an exemplary embodiment of a device for visualization of a functional sequence of a medical apparatus.

FIG. 3 shows an operating room 50 with a plurality of medical devices and an exemplary embodiment of a device 10 for the visualization of a functional sequence of a medical apparatus 30. A medical apparatus 30 (e.g., a two-level X-ray device), in which an X-ray source and an X-ray detector are arranged opposite each other on a C-arm 32, is provided. The C-arm 32 is movably connected to the ceiling of the operating room 50 by a ceiling mount. The two-level X-ray device is used, for example, for the examination of a human patient 42 positioned on a movable patient table 38. Images of the patient 42 may be displayed on a monitor rack 34 that may be positioned by an articulated arm 36. An operator 40 (e.g., a physician) may operate the medical apparatus 30, the patient table 38 and the monitor rack 34 using various control elements such as a foot switch 22, a joystick 28 or an input device 26 (e.g., a keyboard or a touch-sensitive screen) to, for example, alter the position of a component of one of the devices using a motor, set parameters, or obtain X-ray images. The medical devices may also be able to carry out motion or functional sequences automatically or semi-automatically (e.g., for organ programs). The medical apparatus 30 includes an arithmetic and control unit 24 configured, for example, as a computer (e.g., including a processor) or electronic circuit. The arithmetic and control unit 24 controls the medical apparatus. In addition to control signals, such as activation signals for electric motors for the movement of the C-arm 32 or the triggering of an X-ray image, the arithmetic and control unit 24 may also store input signals of the control elements, such as the foot switch 22, the joystick 28 and the input device 26, in a log file. Storage of the electrical signals may, for example, take place at predeterminable times (e.g., ten storage values per second) or when one of the electrical signals is changed. The time of storage is also verified in the log file. The log file may be transmitted to a receiver unit 18 (e.g., also an electronic device for wireless data transmission) with the aid of a transmitter unit 20 (e.g., an electronic device for wireless data transmission). The device 10 according to one or more of the present embodiments includes an arithmetic unit 12 (e.g., a computer including a processor) and an output unit 14 (e.g., a monitor). The arithmetic unit 12 is configured to accept a mathematical model that, for example, describes the medical apparatus 30, the monitor rack 34 and the patient table 38. The mathematical model takes into account, for example, the geometric expansion of the C-arm 32 and permits the calculation of the position of one of the X-ray detectors as a function of electrical control signals such as voltage and current values of electric motors that may move the C-arm 32. In this exemplary embodiment, the mathematical model is stored in a database 16 and may be transferred to a working memory of the arithmetic unit 12 by a loading process. The log file may be accepted by the receiver unit 18. The arithmetic unit 12 is configured to determine at least one state variable of the medical apparatus 30, the monitor rack 34 and the patient table 38 as a function of the mathematical model and the log file using, for example, a computer program that is stored and processed in the working memory of the arithmetic unit 12. A state variable is, for example, the position of one of the X-ray detectors. The arithmetic unit 12 is further configured to convert the determined state variable or the determined state variables of the medical apparatus 30, the monitor rack 34 and the patient table 38 into a visualization signal and to make the visualization signal available to the output unit 14. A visualization signal may be, for example, an output signal of a graphics card that is supplied to the output unit 14 (e.g., the monitor). The output unit 14 is configured to accept and visualize the visualization signal. In the exemplary embodiment of FIG. 3, the mathematical model also includes an object outside the medical apparatus 30 (e.g., the operator 40), and the log file also includes at least one value describing the additional object. Consideration of the additional object may include the geometric dimensions of the operator 40 being modeled by geometric base bodies such as cuboids or cylinders. A value of the log file that describes the additional object may be, for example, a position coordinate of the head of the operator 40. The position coordinate may be obtained by a stereo camera 46 including two individual cameras at a distance from each other or a time-of-flight camera known and supplied to the arithmetic and control unit 24 of the medical apparatus 30. In addition, the mathematical model may include a collision model. The collision model may determine a collision value. The collision value may determine the probability of a collision between the medical apparatus 30 and another object (e.g., the operator 40), the patient table 38 or the monitor rack 34.

Figure 4:
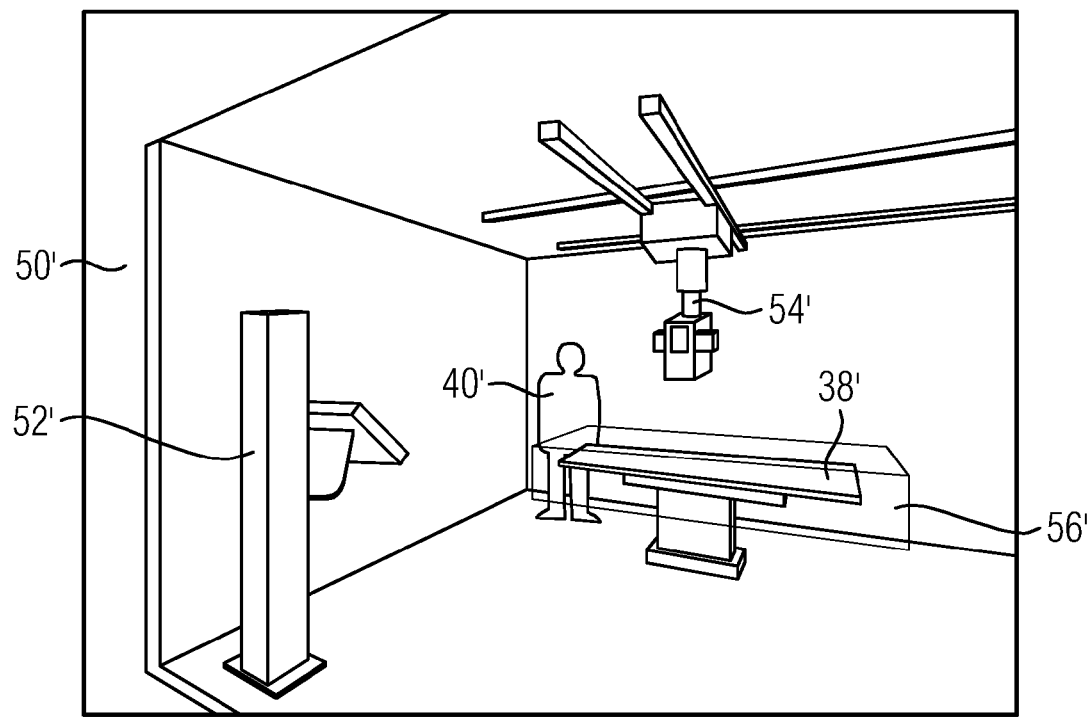
FIG. 4 shows an exemplary embodiment of a visualization of a functional sequence in an operating room with a plurality of medical devices.

FIG. 4 shows an exemplary embodiment of a visualization of a functional sequence in an operating room with a plurality of medical devices, as the visualization may be displayed, for example, on an output unit (e.g., a monitor). The visualization includes a visualization 50' of the operating room, a visualization 54' of a medical apparatus (e.g., an X-ray device that is movably connected to the ceiling of the operating room 50 by a ceiling mount), a visualization 52' of an object outside a medical apparatus (e.g., a control panel of the X-ray device), a visualization 38' of a patient table and the visualization 40' of an operator. In addition, the visualization includes a visualization 56' of a collision area. The collision area indicates, for example, an area of risk around the patient table in which a component of the X-ray device (e.g., an X-ray source assembly) may collide with the patient table.

Figure 5:
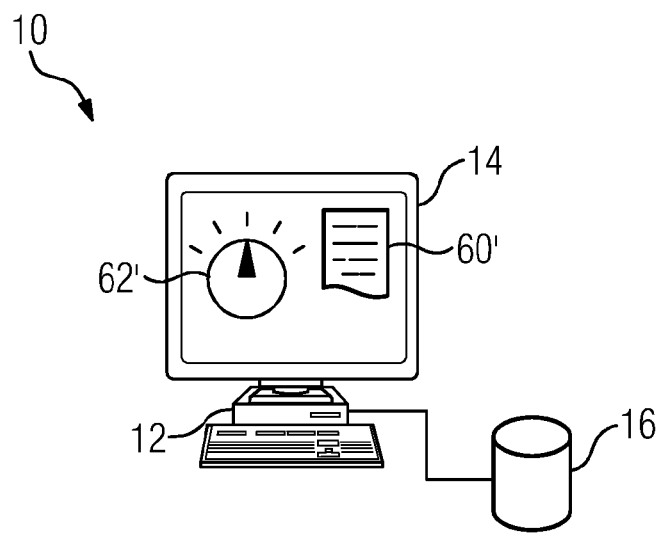
FIG. 5 shows an exemplary embodiment of a visualization of a functional sequence of a medical apparatus.

FIG. 5 shows an exemplary embodiment of a visualization of a functional sequence of a medical apparatus with the aid of a device 10 for the visualization of a functional sequence of a medical apparatus. The device 10 includes an arithmetic unit 12 (e.g., a computer) and an output unit 14 (e.g., a monitor). The arithmetic unit 12 obtains a mathematical model from a database 16 that at least describes the medical apparatus, and a log file that includes at least one value of at least one electrical signal of the medical apparatus during the functional sequence. The arithmetic unit 12 determines at least one state variable of the medical apparatus as a function of the mathematical model and the log file and converts the at least one determined state variable of the medical apparatus into a visualization signal that is made available to the output unit 14. The output unit 14 accepts the visualization signal and displays the visualization. The visualization includes a visualization 60' of a state variable of the medical apparatus as a numerical value and a visualization 62' of a state variable of the medical apparatus in pointer display.

Further embodiments and advantages are described. The service department of an X-ray device manufacturer receives queries from customers concerning a malfunction in an X-ray system or application queries associated with the workflow. An adequate response may not be given at present, as the operator is unable to describe the operating steps precisely, and even an experienced service employee is frequently unable to reproduce this malfunction in the system. It is sometimes possible to reproduce a functional sequence using a time-consuming investigation or evaluation of log files, or AXCS telegrams. One or more of the present embodiments provide a visualization method in which by loading these log files and/or AXCS telegrams and with the aid of a mathematical model, for example, a 3D-visualization of the X-ray system and/or the workflow may be shown over time or at the time of the malfunction. In one embodiment, a presentation of an X-ray system in a 3D-presentation and a visualization of the space and workflow constellation actually offered at the customer's premises are possible, enabling these to be reproduced at any time (e.g., off-line), and a labor-intensive investigation of the problem may thus be avoided.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for visualization of a functional sequence of a medical apparatus, the method comprising:
   receiving a mathematical model describing at least the medical apparatus;
   receiving a log file describing historical parameters of the medical apparatus, wherein the log file comprises at least one value of at least one electrical signal of the medical apparatus during the functional sequence;
   determining, by a processor, at least one state variable of the medical apparatus as a function of the mathematical model and the log file;
   converting the at least one state variable of the medical apparatus into a visualization signal; and
   visualizing the at least one state variable of the medical apparatus, the visualizing of the at least one state variable of the medical apparatus comprising displaying, by an output unit, a graphic image of the mathematical model.

2. The method of claim 1, wherein the medical apparatus comprises an imaging system.

3. The method of claim 1, wherein the log file comprises a time sequence of the at least one value of the at least one electrical signal of the medical apparatus during the functional sequence, and
wherein the determining and the visualizing are repeated for selectable points in time.

4. The method of claim 1, wherein the mathematical model also describes an object outside the medical apparatus.

5. The method of claim 4, wherein the log file further comprises at least one value describing the object outside the medical apparatus.

6. The method of claim 5, further comprising determining, by the processor, a collision value as a function of a collision model of the mathematical model, the collision value determining a probability of a collision between the medical apparatus and the object outside the medical apparatus.

7. The method of claim 4, further comprising determining, by the processor, a collision value as a function of a collision model of the mathematical model, the collision value determining a probability of a collision between the medical apparatus and the object outside the medical apparatus.

8. The method of claim 1, wherein the log file is expanded by a predeterminable value of at least one electrical signal of the medical apparatus, by a value describing the object outside the medical apparatus, or by a combination thereof.

9. The method of claim 1, wherein the medical apparatus comprises an imaging system.

10. The method of claim 9, wherein the log file comprises a time sequence of the at least one value of the at least one electrical signal of the medical apparatus during the functional sequence, and
wherein the determining and the visualizing are repeated for selectable points in time.

11. The method of claim 10, wherein the mathematical model also describes an object outside the medical apparatus.

12. The method of claim 11, wherein the log file further comprises at least one value describing the object outside the medical apparatus.

13. The method of claim 11, further comprising determining, by the processor, a collision value as a function of a collision model of the mathematical model, the collision value determining a probability of a collision between the medical apparatus and the object outside the medical apparatus.

14. A device for visualization of a functional sequence of a medical apparatus, the device comprising:
a processor; and
an output unit,
wherein the processor is configured to:
receive a mathematical model describing at least the medical apparatus;
receive a log file describing historical parameters of the medical apparatus, wherein the log file comprises at least one value of at least one electrical signal of the medical apparatus during the functional sequence;
determine at least one state variable of the medical apparatus as a function of the mathematical model and the log file; and
convert the at least one state variable of the medical apparatus into a visualization signal and make the visualization signal available to the output unit,
wherein the output unit is configured to accept and visualize the visualization signal, and
wherein the output unit is configured to display a graphic image of the mathematic model.

15. The device of claim 14, wherein the medical apparatus comprises an imaging system.

16. The device of claim 14, wherein the log file comprises a time sequence of the at least one value of the at least one electrical signal of the medical apparatus during the functional sequence, and
wherein the determination and the visualization are repeated for selectable points in time.

17. The device of claim 14, wherein the mathematical model also describes an object outside the medical apparatus.

18. The device of claim 17, wherein the log file further comprises at least one value describing the object outside the medical apparatus.

* * * * *